United States Patent [19]
Jeffcoat et al.

[11] Patent Number: 5,318,442
[45] Date of Patent: Jun. 7, 1994

[54] PERIODONTAL PROBE

[75] Inventors: Marjorie K. Jeffcoat, 2109 Countryridge La., Vestavia Hills, Ala. 35216; Albert L. Thomas, Jr., Auburn, Ala.; Robert L. Jeffcoat, Vestavia Hills, Ala.

[73] Assignees: Marjorie K. Jeffcoat, Vestavia Hills; Research Models, Inc., both of Ala. ; a part interest

[21] Appl. No.: 884,921

[22] Filed: May 18, 1992

[51] Int. Cl.5 .................. A61C 19/04; A61B 5/103; A61B 5/117
[52] U.S. Cl. ..................................... 433/72; 128/776; 433/27
[58] Field of Search ............ 433/72, 75, 27, 141, 433/215; 128/776; 33/514, 513

[56] References Cited

U.S. PATENT DOCUMENTS

| | | | |
|---|---|---|---|
| 3,058,225 | 10/1962 | Ward | 128/776 X |
| 3,943,914 | 3/1976 | Grenfell et al. | 433/72 X |
| 4,764,114 | 8/1988 | Jeffcoat et al. | 128/776 X |
| 4,791,940 | 12/1988 | Hirschfeld et al. | 433/72 X |
| 4,960,132 | 10/1990 | Habekost | 433/72 X |
| 4,979,898 | 12/1990 | Rand | 433/72 |
| 5,144,753 | 9/1992 | Murphy | 433/72 X |

OTHER PUBLICATIONS

"Gingival attachment level measurements with an automated periodontal probe" Birek et al. J. Clin. Periodontal 1987; 14:472–477.

Primary Examiner—Gene Mancene
Assistant Examiner—Nicholas A. Lucchesi
Attorney, Agent, or Firm—Veal & Associates

[57] ABSTRACT

An automated periodontal probe uses a logic device to control the drive motor of a distendable probe rod. The movement of the probe rod is measurable and the force applied to the rod is quantifiable, therefore the device affords exacting repeatability of test procedures on periodontal tissues and permits an accurate survey of the gum pockets which survey may be displayed or recorded. Further the device can be calibrated to cause minimum discomfort to the patient.

19 Claims, 5 Drawing Sheets

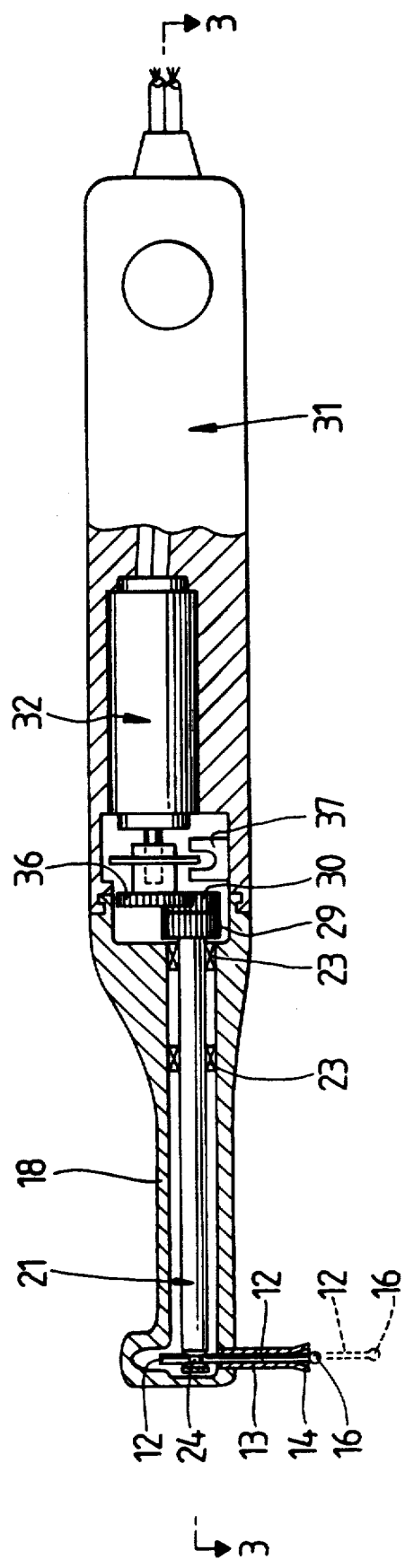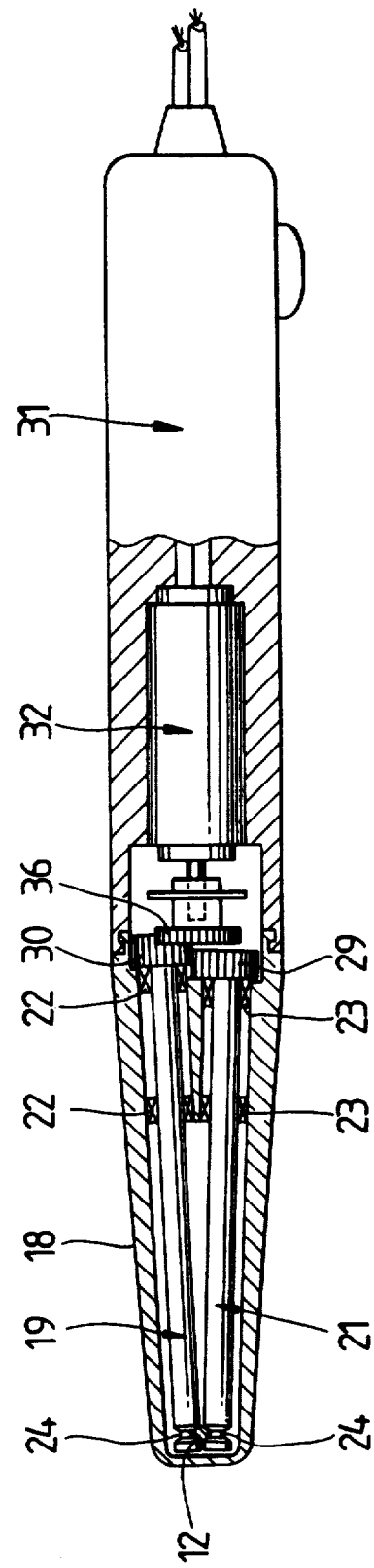

PERIODONTAL PROBE

FIELD OF THE INVENTION

The present invention relates to testing of periodontal or other highly vascular subcutaneous tissue for tendency to bleed when subjected to controlled pressure or stress. More particularly, the present invention relates to an electronic probe for applying pressure of a given value to measure the depth at which organic response is determined. In still greater particularity the invention concerns a distendable probe having a repeatable force application and means for measuring the distention of the probe relative to a reference.

BACKGROUND OF THE INVENTION

In the routine assessment of periodontal tissue suspected of disease a probe consisting of a rod with a round end is pressed into the gum pocket until a sense of resistance is felt, at which point the depth is estimated relative to the rod. In some subjects bleeding occurs readily, indicating less than normal strength of the walls of the capillary vessels and other tissues. However, the force necessary to induce bleeding is subjectively sensed, not measured relative to an objective quantum of force or weight. In subsequent assessments, after treatment, the degree of improvement can be determined only to the extent that the improvement is of a significance greater than the inherent subjectivity of the sense of force applied by the dentist. Thus the efficacy of the treatment has not heretofore been subject to objective measurement.

SUMMARY OF THE INVENTION

It is the principal object of the invention to enable periodontal surveys to be made with a reproducible force of probe and a calibrated measurement of depth at a known force.

A further object of the invention is to provide an instrument that would allow periodontal testing at a selected force level by an operator who did not have the training or ability to quantify the force applied by manual means.

Still another object of the invention is to provide a visually perceptible indication, visible externally of the mouth, of the depth of the periodontal probing relative to a fixed reference and which persists after retraction of the probe.

Yet another object of the invention is to enable the automatic recordation of a series of probe tests to create a profile of the organic response with respect to one or more teeth and the periodontal tissues associated therewith.

Another object of one embodiment of the invention is to enable bacteriological sampling of the tissue during clinical testing of the tissue.

An additional object is to provide a device which accomplishes all of the above, yet which is relatively unobtrusive and does not create significant discomfort or concern in the patient.

These and other objects and features of our invention are readily achieved by the unique combination of elements which interact in our invention.

Our invention utilizes a hand-held instrument which is operatively connected to a logic device which serves as both an input and display device. The logic device is preferentially a programmable computer, but it may be any suitable electronic circuit which is configured to perform the functions as set forth hereinafter.

The hand-held instrument carries a probing rod having an optionally enlarged tip, the rod being mounted for reciprocal axial movement within a coaxial sheath, the sheath having one end configured to engage the cemento-enamel interface of a tooth and being captured at a second end in a housing which has a longitudinal axis perpendicular to the reciprocal motion of the probing rod, and which contains therewithin a pair of elongated pinch rollers which capture the probing rod therebetween so as to cause the reciprocal motion thereof by the concomitant rotation of the pinch rollers, when driven by an actuator such as a small electric motor contained in a detachable housing which also forms a portion of the instrument, with the actuator being operable responsive to signals received through the logic device and including sensing means which indicate to the logic device the depth of extension of the probing rod.

BRIEF DESCRIPTION OF THE DRAWINGS

Apparatus embodying features of our invention are depicted in the accompanying drawings which form a portion of this disclosure, in which

FIG. 2 is a side elevational view of the hand-held instrument with the outer housing components removed;

FIG. 3 is a sectional view taken along line 3—3 of FIG. 2;

DESCRIPTION OF THE PREFERRED EMBODIMENT

Figure 1:
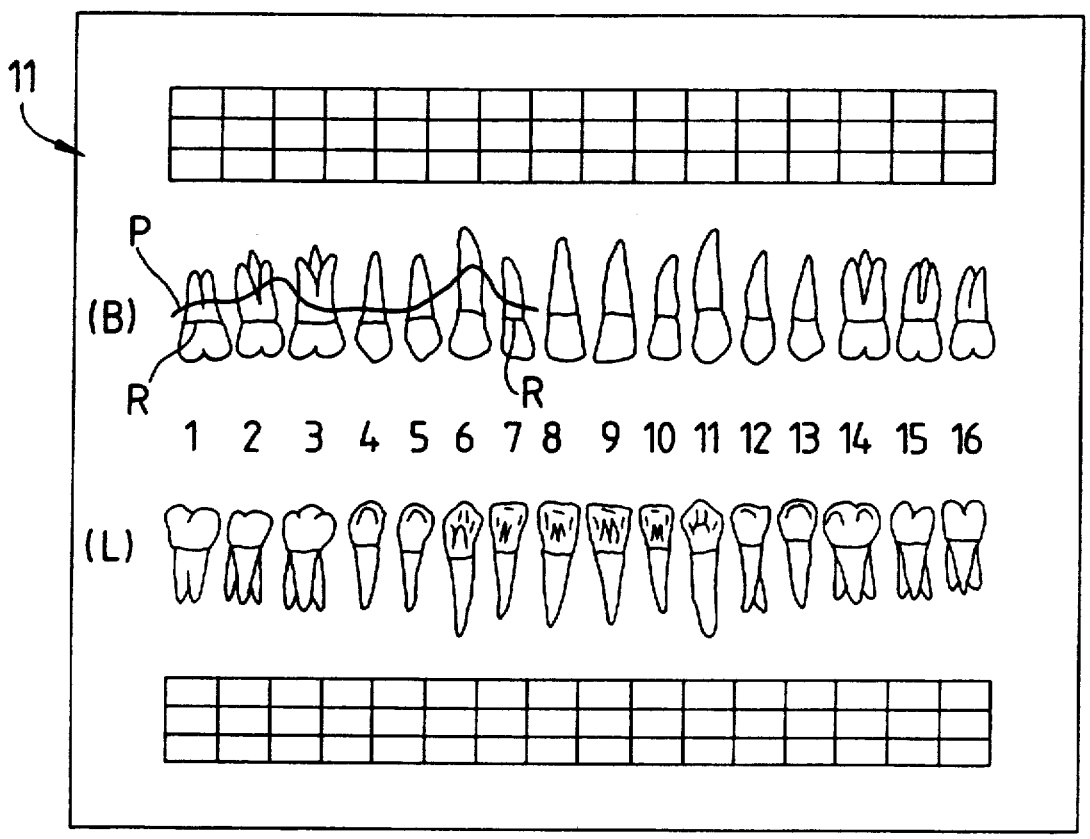
FIG. 1 is the output of a display indicating the depth of probing rod insertion relative to the cemento-enamel junction.
Figure 6:
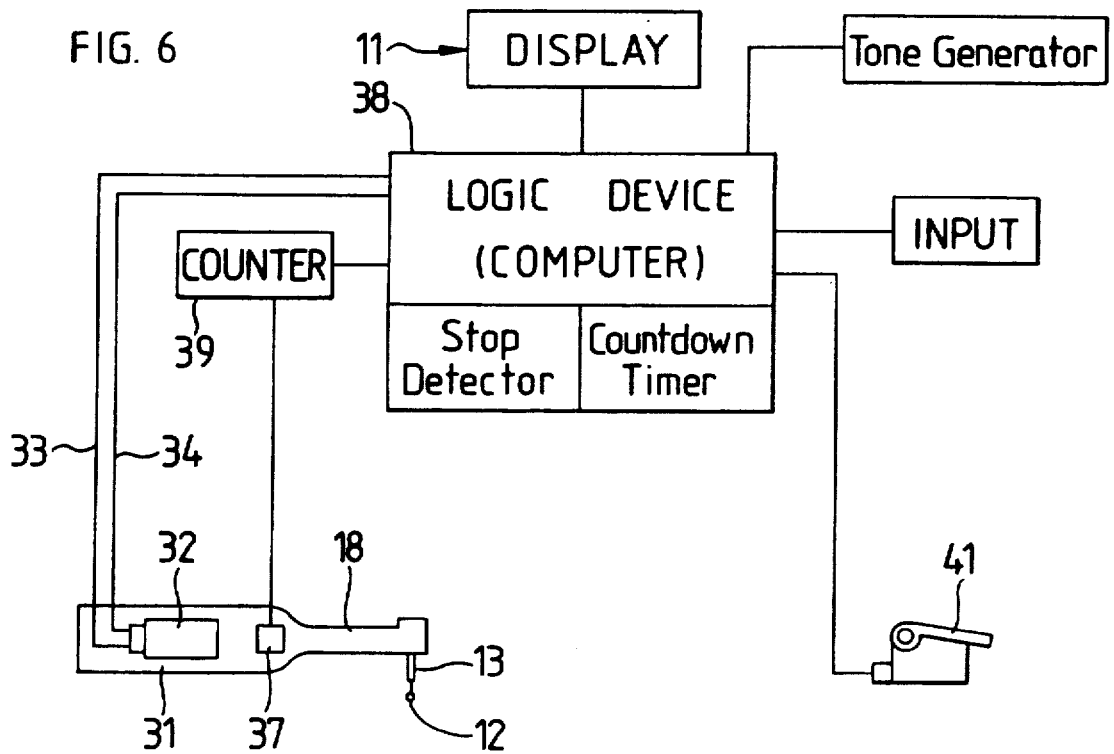
FIG. 6 is a block diagram of the components of the apparatus.

Referring to the drawings for a clearer understanding of the invention, it may be seen that FIG. 1 represents a computer screen 11 on which a display is presented. The particular display is a pictorial representation of the front (B) and rear (L) view of the upper teeth of a patient's mouth. Across each representation of a tooth a line R is indicated, which illustrates the cemento-enamel junction, which is the reference against which periodontal probing for organic disease is preferably measured. It will be appreciated by those skilled in the art that the pictorial form of illustration is but one form which could be used within the scope of the invention. For example, the pictorial illustration could be replaced by a bar graph or by merely a numerical value relative to the established reference. Likewise, the method of presentation could be a chart printed on paper as well as a video or computer screen. Regardless of the specific manner of presentation, the invention is intended to yield specific data regarding the health of the tissue surrounding each tooth. That data may be presented in one form by the line P on FIG. 1 which indicates probe depth relative to R.

Figure 5:
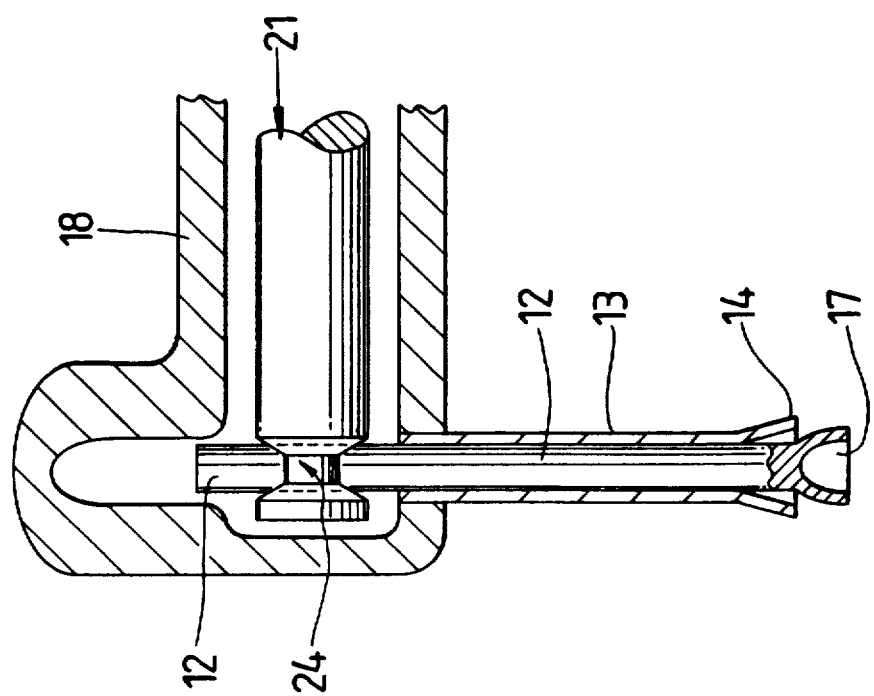
FIG. 5 is a detail view of an alternative embodiment of the probing rod.
Figure 4:
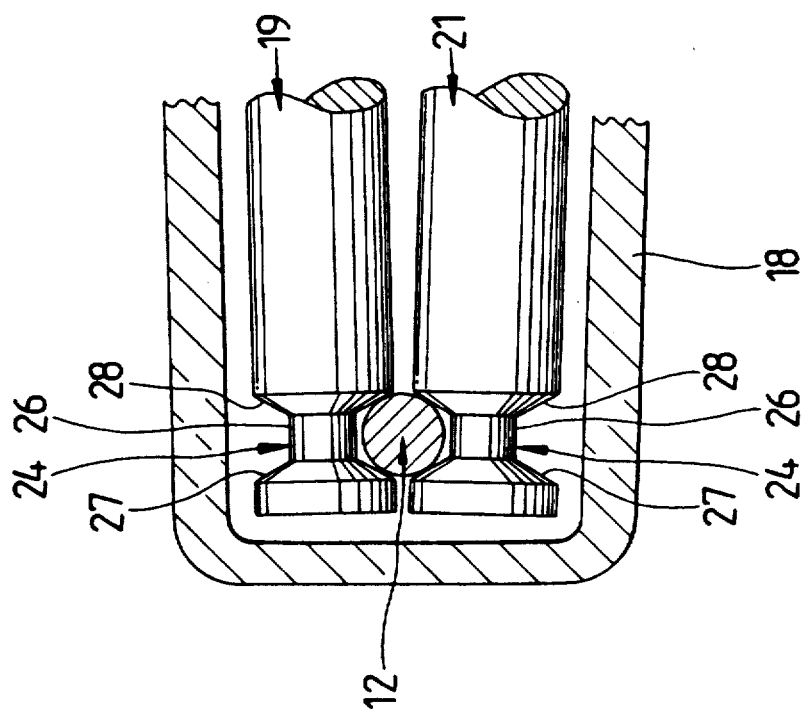
FIG. 4 is a detail view of the end of the pinch rollers engaging the probing rod.

Referring to FIGS. 2-4, it may be seen that the points along line P are generated by the distention of probing rod 12 from sheath 13 and the measurement of that distention. Sheath 13 may be flared at its terminus 14 such that an outwardly extending component thereof is used by the operator to feel and engage the cementoenamel interface of the tooth and thus establish the reference against which probing rod distention is measured. The probing rod 12 may be made to terminate in an enlarged rounded portion 16 as seen in FIGS. 2 and 3 or a cup portion 17 as seen in FIG. 5, such that the rod 12 cannot be fully retracted into the sheath 13. The remainder of probing rod 12 has a constant diameter and is preferably a smooth elongated rod which extends through sheath 13 into housing 18. Housing 18 extends generally perpendicular to sheath 13 and engages sheath 13 to hold it in fixed relation. The housing includes an internal cavity sufficiently large to permit probing rod 12 to be fully retracted into sheath 1 without interference.

Mounted within housing 18 are a pair of pinch rollers 19 and 21 supported for rotation on bearings 22 and 23, respectively. As shown in FIGS. 2-4, each pinch roller may have a circumferential groove 24 formed in one end thereof within which the probing rod 12 is received. The detail view of the grooves 24 in FIG. 4 shows the grooves 24 to be formed by a reduced diameter annulus 26 and a pair of opposed conic surfaces 27 and 28. The inclination of the conic surfaces is intended to provide a predetermined gripping force to the probing rod 12 such that excessive force cannot be applied to the rod by rotation of the pinch rollers. Tensioning means are provided to control the pressure applied to the rod by the pinch rollers. In a preferred embodiment, the diameter of the rollers themselves between grooves 24 and bearings 22 and 23 and their material, typically stainless steel for autoclaving purposes, is chosen to provide a degree for flexure that will prevent excessive force transfer to the probing rod. In this embodiment, the grooved ends of the pinch rollers 19 and 21 are not supported in bearings but rather are free standing. The ends of pinch rollers 19 and 21 opposite the grooved ends carry intermeshed gears 29, one of which may be a drive gear 30 such that the rollers may be driven for concomitant counter-rotating movement via drive gear 30. Any suitable means for conducting this rotation is acceptable. The housing 18 encloses and supports the rollers 19 and 21 and the end of sheath 13 and is detachably affixed to a handle portion 31 which is also a housing for a motor 32 powered by an external source through lead lines 33 and 34. The motor may be any suitable device, i.e. electric, pneumatic, or hydraulic, however an electric motor will be presumed throughout this description to assure clarity in presentation. Obviously, if another type motor is used, specific changes in the control aspects will be understood by those skilled in the art. Housing 18 may be detached from handle portion 31 and sterilized as by autoclaving or other suitable means and reattached to handle portion 31 for reuse.

Motor 32 has an output gear 36 which meshes with drive gear 30 to selectively rotate the pinch rollers 19 and 21 such that probing rod 12 will be distended or retracted within sheath 13. The distention of the probing rod 12 has a known relationship to the rotation of the motor therefore an encoder 37 may be used to generate a signal determinative of the number of revolutions of the motor or output gear, which signal may then be processed by the logic system 38.

The logic system includes a counter 39 which receives the signals from the encoder 37 and outputs an associated signal to further components such as a programmable computer or to a driver for a display. The driver for a display would generate a visual signal on an LED or other device that would yield a calibrated indication of the distention of the probe. It should be understood that the motor 32 is not continuously running but rather is operative responsive to a voltage waveform from a generator in the logic circuit. This voltage waveform is preferentially a square wave whose amplitude and period may be selectively varied to vary the operation of the probe. For example, a low voltage long duration waveform would be used to provide a low force, low speed distention of the probing rod, whereas a higher voltage shorter duration waveform would yield a more forceful, more rapid distention of the probing rod. In both cases the retraction period is longer than the distention period. By controlling the waveform in discrete voltage steps and discrete periods, discrete levels of force may be applied to the probing rod. With the knowledge of the period of distention, it is clear that the encoder signals can be used to determine whether the probing rod traveled to the full extension expected or whether its travel was arrested earlier than expected. Likewise, if the distention continues after a preset period which would indicate normal distention, a continuing signal from the encoder would be recorded on the counter to indicate an abnormal depth in the pocket.

Figure 7:
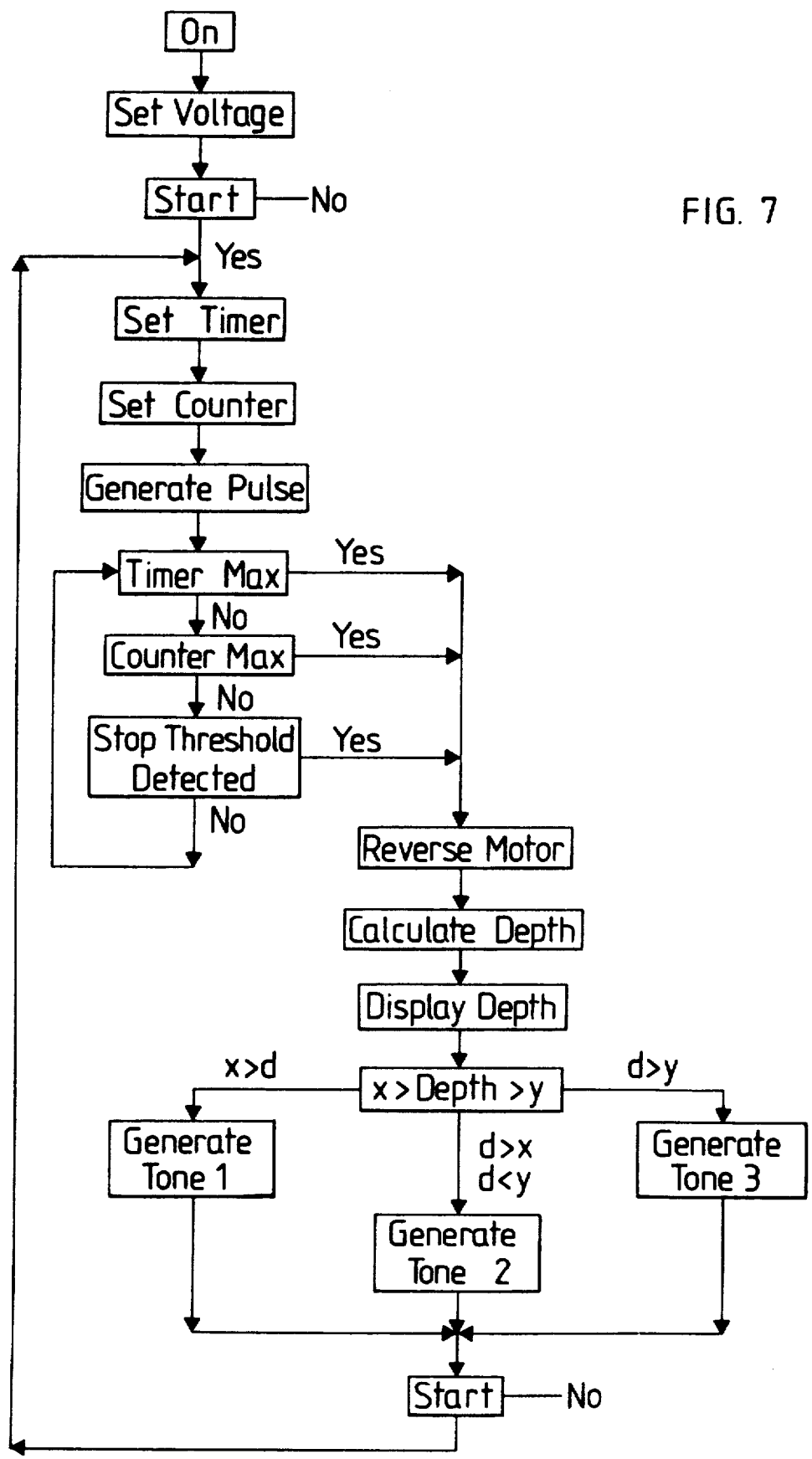
FIG. 7 is a generalized flow chart of the methodology of the device.
Figure 8:
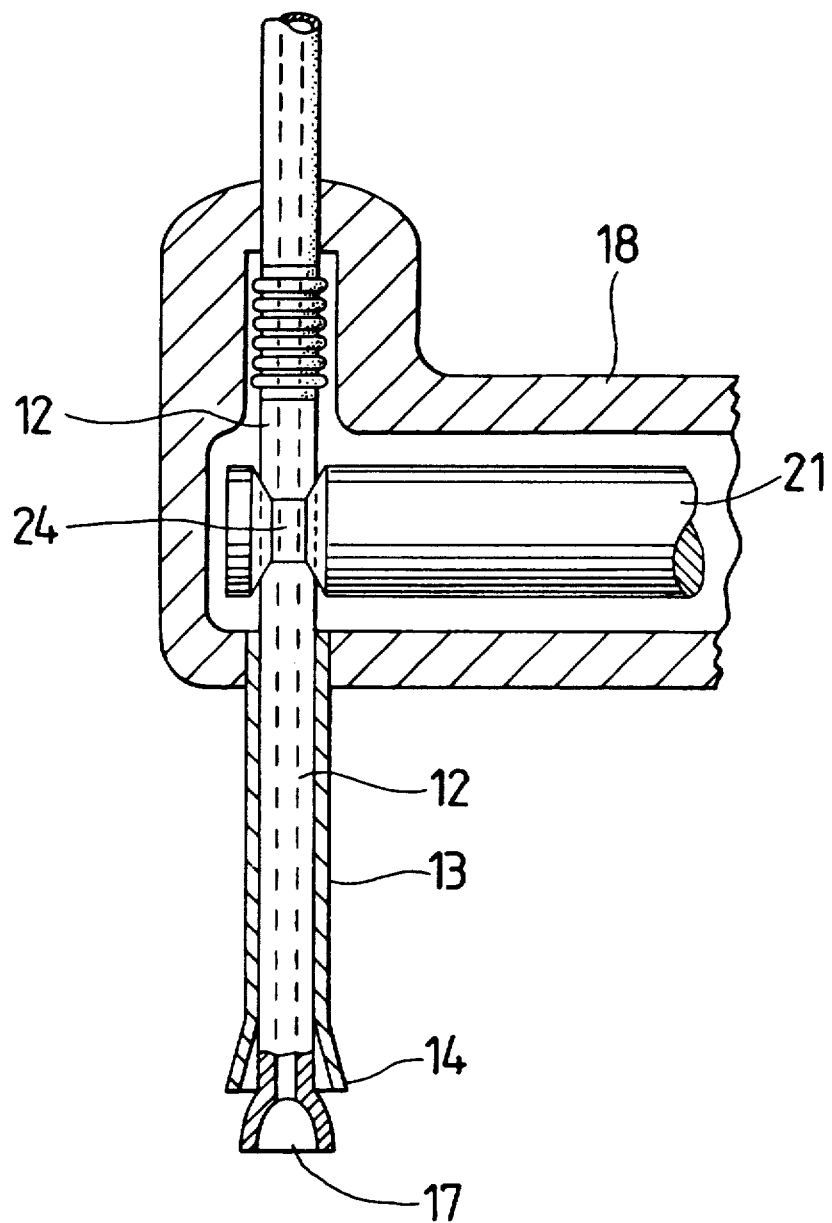
FIG. 8 shows a tubular probe rod.

The foregoing aspects of the invention are more fully explained with reference to FIG. 7 and the following description of the utilization of the invention in conjunction with FIGS. 1-5. The dentist or technician would first input via the logic system or computer a probe drive voltage. That is to say, the shape of the voltage waveform would be selected from a predetermined number of variations which have been programmed into the logic system. Responsive to this input a selected voltage would be available to drive the motor, and a preset maximum distention duration would be established. Also, a preset retraction duration would be established and a visual display of the "force" level would be presented to the operator. The operator may select another voltage which would change each of the above responses.

If a computer is used in or as the logic system, it may be preprogrammed to assist in record keeping. Otherwise recording data could be directly printed in chart form or transcribed by hand. For the purposes of clarity of this disclosure it will be assumed that a computer will record and display various data items. Specifically each tooth is assigned a location code as seen in FIG. 1. Additionally, six samples of the periodontal tissue will be made at different locations relative to each tooth. The dentist or technician will input to the computer the code for the tooth and sample under test or will begin testing at a certain tooth and follow a sequence previously input into the computer.

The operator would then input a command to begin recording data. Typically a footswitch 41, of the type commonly used by dentists, would then be used to indicate to the logic system that the operator had positioned the instrument adjacent the tooth and initiate a probe distention. To position the instrument, the operator moves the sheath 13 along the tooth until the flared edge of the sheath is aligned with the cemento-enamel junction, which is readily felt by the operator. Depression of the footswitch initiates a sequence in the logic circuit which first clears any prior data. An appropriate voltage waveform is generated and sent to the motor. The counter is enabled to determine how far the probe rod is distended; a stop detector is enabled to determine when the encoder has stopped sending data thus indicating that the probe has stopped; a countdown timer is enabled for a period dependent on the voltage waveform. The stop detector or the timer will generate a signal to reverse the motor to retract the probe. When either of these signals is generated, the counter will display the depth or distention visually to the operator via display 11 or other visual or audible means. As a further aid to the operator the value of the depth count may be converted to a scale familiar to the dentist, millimeters. Each measurement may be sorted into ranges of depth such as shallow, normal, abnormal, and very deep, and the computer can be programmed to sound a series of tones corresponding to the range into which a reading has been sorted. Thus, without looking away from the patient, the dentist can be aware of a most significant probing event. The depth and voltage level for the Tooth No. and Sample No. will be recorded in memory or on a hard copy, and/or displayed on display 11. For example, the computer may use the data points in a sequence to draw line P or may display discrete plots of the data points. The operator may then reposition the instrument to the next sample position and depress the footswitch to obtain and record data at that location.

FIG. 4 shows a probing rod which has been modified to allow further testing by removing a small sample of bacteria living in the pocket within the cup-like receptacle found in the rod terminus. The rod may also be tubular to permit the injection or retraction of fluid therethrough by a suitable connection to a fluid pump. It should further be noted that the probe rod may be made from steel or plastic to yield maximum efficiency without damaging natural or surgically implanted teeth. It should further be noted that the ability to quantitatively apply force along with the rounded probe tip allows the dentist to replicate an examination identically without undue discomfort or guesswork as to the force applied. Furthermore the stop detector can indicate not only a complete stop but also a significant reduction in the rate of advance of the probe such as will occur when the probe encounters resistive tissue at the bottom of the gum pocket. The logic device may be set to reverse the motor and retract the probe when such resistance is encountered. Accordingly, minimal discomfort to the patient is achieved.

While we have shown our invention in one form, it will be obvious to those skilled in the art that it is not so limited but is susceptible of various changes and modifications without departing from the spirit thereof.

What we claim is:

1. Apparatus for calibrated testing of highly vascular subcutaneous tissue for organic response when subjected to controlled pressure comprising:
   (a) a probing rod mounted for controlled distention and retraction relative to a coaxial sheath;
   (b) drive means for controlled distention and retraction of said probing rod, said drive means comprising a pair of pinch rollers engaging said probing rod therebetween in perpendicular relation thereto, and means for driving said pinch rollers in selected counter-rotating directions to distend and retract said probing rod;
   (c) sensing means associated with said drive means for indirectly sensing the distention of said probing rod and outputting a signal in accordance therewith;
   (d) control means for selectively varying the force applied by said probing rod at said tissue and outputting a signal in accordance therewith; and
   (e) programmable means for calibrating, recording, and displaying parameters associated with said signals from said sensing means and said control means.

2. Apparatus as defined in claim 1 wherein said pinch rollers are rotatably mounted in independent bearings distal said probing rod, said probing rod being engaged proximal an end of said pinch rollers.

3. Apparatus as defined in claim 2 wherein each of said pinch rollers have a circumferential groove formed therein and said probing rod is engaged within each said circumferential groove.

4. Apparatus as defined in claim 1 wherein each of said pinch rollers have a circumferential groove formed therein and said probing rod is engaged within each said circumferential groove.

5. Apparatus as defined in claim 1 wherein said means for driving comprises an electric motor mounted within a housing which serves as a handle for manipulation of said probing rod by a user, said probing rod and said pinch rollers being supported within a separate housing detachably affixed to said handle.

6. Apparatus as defined in claim 1 wherein said probing rod is substantially tubular to permit a fluid to be continuously or intermittently introduced into or removed from the vicinity of the subcutaneous tissue for diagnostic or therapeutic purposes.

7. Apparatus for calibrated testing of highly vascular subcutaneous tissue for organic response when subjected to controlled pressure comprising:
   (a) a probing rod mounted for controlled distention and retention relative to a coaxial sheath;
   (b) drive means for controlled distention and retraction of said probing rod, said drive means comprising a pair of pinch rollers engaging said probing rod therebetween in perpendicular relation thereto, and means for driving said pinch rollers in selected counter-rotating directions to distend and retract said probing rod comprising an electric motor mounted in a housing which serves as a handle for manipulation of said probing rod by a user, said probing rod being supported by a separate housing detachably affixed to said handle.
   (c) sensing means associated with said drive means for indirectly sensing the distention of said probing rod and outputting a signal in accordance therewith;
   (d) control means for selectively varying the force applied by said probe at said tissue and outputting a signal in accordance therewith; and
   (e) programmable means for calibrating, recording, and displaying parameters associated with said signals from said sensing means and said control means.

8. Apparatus as defined in claim 7 wherein said sensing means comprises an encoder operatively connected to said electric motor to determine the rotation thereof during distention of said probing rod.

9. Apparatus as defined in claim 8 wherein said control means comprises electrical means for varying the duration and voltage of the electrical energy supplied to said motor during said distention of said probing rod.

10. Apparatus as defined in claim 7 wherein said control means comprises electrical means for varying the duration and voltage of the electrical energy supplied to said motor during said distention of said probing rod.

11. Apparatus as defined in claim 10 wherein said programmable means comprises a computer having data input means from said sensing means and control outputs to said sensing means, said control means and an interface means for receiving instruction from an operator, said computer being programmed to quantify said signal from said sensing means as a length of distention of said probing rod from said sheath.

12. Apparatus as defined in claim 11 wherein said programmable means comprises a visual display wherein the amount of distention from a known reference for successive tests is presented in accordance with signals output from said computer.

13. Apparatus as defined in claim 11 wherein said control means further comprises logic means for detecting the first occurrence of either the elapse of a predetermined period of time, a preset maximum distention, or a threshold of cessation of the distention as the probe tip encounters resistance from tissue, so that said probe rod may be retracted responsive thereto.

14. Apparatus as defined in claim 13 wherein said logic means is responsive in sequence to initiation of distention, achievement of a suitable velocity of distention, and detection of a preset reduction in said suitable velocity, which event indicates the probe tip has encountered the subject tissue at the bottom of the gum pocket.

15. Apparatus as defined in claim 11 wherein programmable means for indicating amount of distention is converted to an audible signal to indicate to an operator said distention.

16. Apparatus as defined in claim 7 wherein said coaxial sheath is elongated and includes a terminus which is engageable with the cemento-enamel junction of a tooth to define a reference line for said distention of said probing rod during testing.

17. Apparatus as defined in claim 7 wherein said probing rod has an enlarged diameter end portion having a diameter greater than the inside diameter of said coaxial sheath.

18. Apparatus as defined in claim 17 wherein said enlarged diameter end portion is tubular and open at an end distal said coaxial sheath for extracting a bacterial sample therein from said subcutaneous tissue.

19. A method of testing subcutaneous periodontal tissue comprising locating the cemento-enamel junction with an instrument, iteratively distending a probe rod from said instrument into the gum pocket at a preset force through the use of a drive means comprised of a pair of pinch rollers engaging said probe rod therebetween in perpendicular relation and retracting said probe rod responsive to the first occurrence of either the elapse of a preset time period, a preset maximum distention of said rod, or retardation of said distention by tissue at the bottom of the gum pocket, automatically measuring the distention of said probe rod automatically displaying said distention and said preset force for each iterative distention to indicate the profile of said gum pocket.

* * * * *